(12) United States Patent
Kim

(10) Patent No.: US 11,806,124 B2
(45) Date of Patent: Nov. 7, 2023

(54) METHOD AND APPARATUS FOR MEASURING SIGNAL

(71) Applicant: Samsung Electronics Co., Ltd., Suwon-si (KR)

(72) Inventor: JongPal Kim, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 512 days.

(21) Appl. No.: 16/655,817

(22) Filed: Oct. 17, 2019

(65) Prior Publication Data

US 2020/0352471 A1 Nov. 12, 2020

(30) Foreign Application Priority Data

May 7, 2019 (KR) ........................ 10-2019-0053093

(51) Int. Cl.
| | |
|---|---|
| *A61B 5/053* | (2021.01) |
| *H03F 3/45* | (2006.01) |
| *H03M 1/12* | (2006.01) |
| *A61B 5/00* | (2006.01) |

(52) U.S. Cl.
CPC ............ *A61B 5/053* (2013.01); *A61B 5/7225* (2013.01); *H03F 3/45071* (2013.01); *H03M 1/124* (2013.01); *H03F 2200/129* (2013.01); *H03F 2200/228* (2013.01); *H03F 2203/45116* (2013.01)

(58) Field of Classification Search
CPC ...... A61B 5/053; A61B 5/7225; H03M 1/124; H03F 3/45071; H03F 2200/129; H03F 2200/228; H03F 2203/45116

USPC ........................................................ 330/252
See application file for complete search history.

(56) References Cited

U.S. PATENT DOCUMENTS

| | | | |
|---|---|---|---|
| 7,622,988 B2 | 11/2009 | Denison et al. | |
| 8,412,317 B2 | 4/2013 | Mazar | |
| 9,197,173 B2 | 11/2015 | Denison et al. | |
| 9,204,816 B2 | 12/2015 | Aga | |
| 10,022,064 B2 | 7/2018 | Kim et al. | |
| 10,041,929 B2 | 8/2018 | Just et al. | |
| 10,892,722 B2 * | 1/2021 | Hurwitz ................. | G01R 17/00 |
| 2012/0123232 A1 * | 5/2012 | Najarian .............. | A61B 5/7203 |
| | | | 600/345 |
| 2016/0142028 A1 * | 5/2016 | Kim ........................ | H03F 3/082 |
| | | | 330/253 |
| 2017/0007186 A1 | 1/2017 | Baek et al. | |
| 2017/0086702 A1 * | 3/2017 | Kim ....................... | A61B 5/053 |

(Continued)

FOREIGN PATENT DOCUMENTS

| | | |
|---|---|---|
| JP | 2017-67641 A | 4/2017 |
| KR | 10-2015-0025109 A | 3/2015 |

(Continued)

*Primary Examiner* — Alex M Valvis
*Assistant Examiner* — Chanel J Jhin
(74) *Attorney, Agent, or Firm* — NSIP Law

(57) ABSTRACT

A signal measuring apparatus and method is provided. The signal measuring apparatus inputs a reduced voltage signal to an input end of an amplifier by resetting a voltage signal, which is acquired by applying a known current signal to a target object, using a common mode voltage at least once during one period of a current signal. The signal measuring apparatus acquires a digital signal corresponding to an object impedance change by converting an output of the amplifier.

17 Claims, 11 Drawing Sheets

(56) References Cited

U.S. PATENT DOCUMENTS

2018/0153432 A1 6/2018 Skrabal et al.
2019/0187734 A1* 6/2019 Kim .................... H03F 3/45475

FOREIGN PATENT DOCUMENTS

| KR | 10-1764603 B1 | 8/2017 |
| WO | WO 90/01670 A1 | 2/1990 |

* cited by examiner

METHOD AND APPARATUS FOR MEASURING SIGNAL

CROSS-REFERENCE TO RELATED APPLICATIONS

This application claims the benefit under 35 USC § 119(a) of Korean Patent Application No. 10-2019-0053093 filed on May 7, 2019 in the Korean Intellectual Property Office, the entire disclosure of which is incorporated herein by reference for all purposes.

BACKGROUND

Field

The following description relates to technology for measuring a signal.

Description of Related Art

A variety of medical devices are being developed to diagnose health conditions of patients. Some of these medical device measure electrical bio-signals of patients to provide a convenient and prompt result of medical checkup.

Among bio-signals, bioimpedance may be used for monitoring the health or emotional state of a living body. In recent years, research is being conducted to miniaturize a bio-impedance measuring apparatus and to measure bioimpedance quickly and accurately.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided an apparatus for measuring a signal, the apparatus including a power source configured to supply a current signal having a carrier frequency to a target object, a reset unit configured to reset an input voltage signal, which is changed according to a change in an object voltage signal generated from the target object receiving the current signal, to have a common mode voltage at least once during a period corresponding to the carrier frequency, and an amplifier configured to generate an amplified signal by amplifying the input voltage signal.

The reset unit may include a capacitor configured to connect the target object and the amplifier, and a reset switch configured to connect one end of the capacitor and a common mode node that supplies the common mode voltage.

The apparatus may include an analog-to-digital converter connected to an output end of the amplifier.

The analog-to-digital converter may be configured to output a digital signal indicating an impedance change of the target object by converting the amplified signal to a digital form.

The apparatus may include a clock generator configured to transfer a carrier frequency to the power source and to transfer a reset signal to the reset unit, wherein the reset unit may be configured to reset the input voltage signal to a common mode signal in response to the reset signal being transferred from the clock generator, and wherein the amplifier may be configured to receive the input voltage signal that may be changed according to a change in the object voltage signal after being reset.

The reset unit may be configured to reset the input voltage signal to have the common mode voltage during a reset interval determined in the period.

The apparatus may include a clock generator configured to transfer a reset signal during the reset interval, wherein the reset unit may include a reset switch configured to connect an input end of the amplifier and a common mode node during a reset interval, in response to the reset signal and to disconnect the common mode node from the input end of the amplifier, in response to the reset interval elapsing.

The reset unit may be configured to disconnect the common mode node from the input end of the amplifier during an interval including a resistance measuring time point and to disconnect the common mode node from the input end of the amplifier during an interval including a reactance measuring time point.

The apparatus may include an analog-to-digital converter configured to generate a digital signal corresponding to a resistance value among impedances of the target object by converting the amplified signal to a digital form at the resistance measuring time point, and to generate a digital signal corresponding to a reactance value among impedances of the target object by converting the amplified signal to a digital form at the reactance measuring time point.

The reset unit may be configured to reset the input voltage signal to have the common mode voltage each time an amplified signal output from the amplifier reaches a threshold voltage.

The apparatus may include an amplitude detector configured to compare an amplitude of the amplified signal and the threshold voltage and to transfer a touch indication signal to a clock generator in response to the amplitude of the amplified signal reaching the threshold voltage, and a clock generator configured to generate the reset signal, in response to the touch indication signal, wherein the reset unit may be configured to connect an input end of the amplifier and a common mode node in response to the reset signal during the period and to disconnect the common mode node from the input end of the amplifier during a remaining interval of the period.

The apparatus may be configured to count a touch number of times that an amplitude of the amplified signal touches the threshold voltage and to calculate an original amplitude of the amplified signal from the counted touch number and the threshold voltage.

The apparatus may include an analog-to-digital converter configured to generate a digital signal corresponding to a resistance value among impedances of the target object by converting the amplified signal to a digital form at a resistance measuring time point, and to generate a digital signal corresponding to a reactance value among impedances of the target object by converting the amplified signal to a digital form at a reactance measuring time point.

The amplifier may include a differential amplifier, and the apparatus may include a chopper circuit connected to an output end of the differential amplifier, a sample and hold circuit connected to an output end of the chopper circuit, and an analog-to-digital circuit connected to an output end of the sample and hold circuit.

The chopper circuit may be configured to generate a chopper voltage signal by alternately switching connections between two output nodes of the amplifier and two input nodes of the sample and hold circuit each half period of the carrier frequency.

The sample and hold circuit may be configured to generate a discrete signal by sampling the chopper voltage signal during a sampling interval in the period and to hold a sampled signal during a holding interval, the sampling interval may be an interval before each measurement time point in the period, and the holding interval may be an interval after each measurement time point in the period.

The analog-to-digital circuit may be configured to convert a differential discrete signal between a first discrete signal and a second discrete signal output from the sample and hold circuit to a digital signal.

In another general aspect, there is provided a method of measuring a signal, the method including supplying a current signal having a carrier frequency to a target object, resetting an input voltage signal, which is changed according to a change in an object voltage signal generated from the target object receiving the current signal, to have a common mode voltage at least once during a period corresponding to the carrier frequency, and generating an amplified signal corresponding to an impedance change of the target object by amplifying the input voltage signal.

Other features and aspects will be apparent from the following detailed description, the drawings, and the claims.

Figure 1:
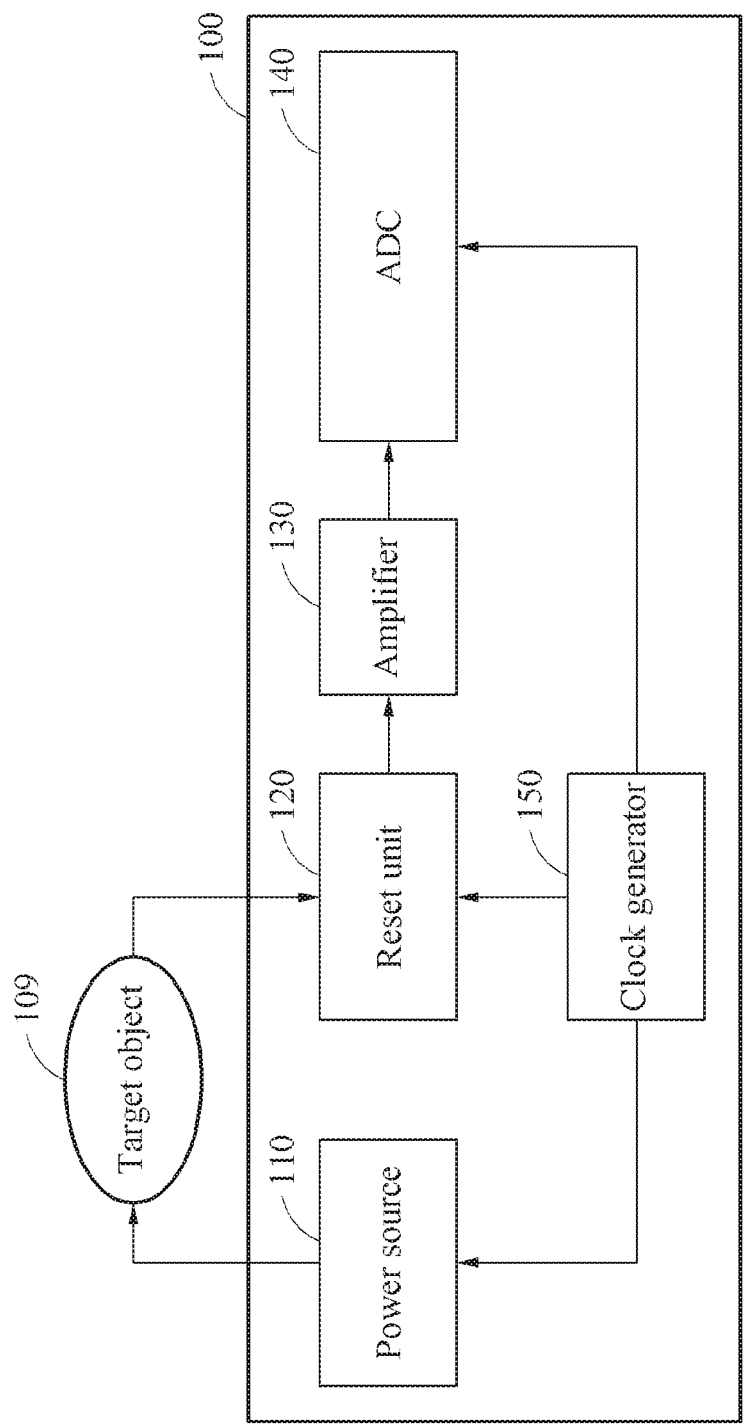
FIG. 1 illustrates an example of a signal measuring apparatus.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

The terminology used herein is for describing various examples only, and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

Also, in the description of embodiments, detailed description of well-known related structures or functions will be omitted when it is deemed that such description will cause ambiguous interpretation of the present disclosure.

FIG. 1 is a diagram illustrating an example of a signal measuring apparatus.

A signal measuring apparatus 100 measures a signal from a target object 109. The target object 109 is, for example, a living body. The signal measured from the living body may be referred to as a bio-signal. The bio-signal may vary based on a biological activity, for example, respiration and a biological condition. In an example, the measured bio-signal is used to determine a condition of the living body. The bio-signal is, for example, a bio-electric signal and a bio-impedance signal. The signal measuring apparatus 100 measures a signal indicating an impedance change of the target object 109, for example, a bioimpedance signal. In the following description, an example of the signal measuring apparatus 100 measuring an impedance signal of the target object 109 is mainly explained. However, other signals may be measured without departing from the spirit and scope of the illustrative examples described. In an example, the signal measuring apparatus 100 measures another electrical signal associated with the target object 109.

The signal measuring apparatus 100 supplies a power signal, for example, a current signal to the target object 109 and measures an electrical signal, for example, a voltage signal triggered in response to the supplied power signal, thereby measuring an impedance of the target object 109. According to Ohm's law, $Z=V/I$ in which Z is an impedance, V is a voltage, and I is a current. In this example, since the voltage V is measured and the current I is given, the signal measuring apparatus 100 acquires the impedance Z.

The signal measuring apparatus 100 includes a power source 110, a reset unit 120, an amplifier 130, an analog-to-digital converter (ADC) 140, and a clock generator 150.

The power source 110 supplies a signal having a carrier frequency to the target object 109. For example, the power source 110 supplies, to the target object 109, a current signal having a waveform of a known amplitude and the carrier frequency. An amplitude of the current signal may be constant value and is not limited thereto. Also, a waveform of the current signal may be sine wave and is not limited thereto.

In an example, the reset unit 120 resets an input voltage signal, which is changed according to a change in an object voltage signal generated from the target object 109 receiving the current signal, to have a common mode voltage at least once during a period corresponding to the carrier frequency. An object signal refers to a signal triggered from an object by a signal supplied from the power source 110. An object voltage signal refers to a signal indicating a voltage applied to the target object 109 when a current signal is applied by the power source 110 to the target object 109. An input voltage signal refers to a voltage signal that changes following a change in the object voltage signal. For example, when the input voltage signal is reset, the input voltage signal may have the common mode voltage at a point in time at which the input voltage signal is reset and change following a change in the object voltage signal from the common mode voltage after the reset. Through this, the reset unit 120 reduces an amplitude of the input voltage signal. A relationship between the object voltage signal and the input voltage signal will be described with reference to FIGS. 4, 6, and 8.

The amplifier 130 generates an amplified signal by amplifying the input voltage signal. The amplifier 130 receives the input voltage signal from the reset unit 120. In the following, the amplifier 130 is mainly described as a full differential amplifier, but is not limited thereto. The amplifier 130 may operate as a single-end mode to receive a single input and generate a single output, or receive a differential input and generate a single output.

Since a magnitude of a voltage input by the reset unit 120 to the amplifier 130 is reduced, a performance required for the amplifier 130 may be reduced. In an example, when two signals are input to the differential amplifier 130, the differential amplifier 130 may output only a differential mode signal indicating a difference between the two signals. However, when a common input signal having a relatively large magnitude of voltage is input to two input terminals of the differential amplifier 130, a differential signal following the common input signal may be generated in an output of the differential amplifier 130, which may lead to an error. As the magnitude of the voltage of the common input signal input to the differential amplifier 130 increases, an error due to such common mode component may increase. A degree of rejecting the common mode component is referred to as a common-mode rejection ratio (CMRR). In the signal measuring apparatus 100, since the reset unit 120 reduces the amplitude of the input voltage signal input to the amplifier 130, the common mode component may be reduced in the output of the amplifier 130 even when the amplifier 130 has a relatively low CMRR. In addition, since the amplitude and the voltage input to the amplifier 130 are reduced, an input voltage range required for the amplifier 130 may also be reduced. Furthermore, a linear performance required for the amplifier 130 may also be reduced. Since the input voltage is reduced, in an example, the amplifier 130 may be designed to have a larger gain. When the amplitude and the voltage input to the amplifier 130 are reduced, a probability that the input voltage and the output voltage are saturated may be reduced, and thus, a distortion in the amplifier 130 may also be reduced.

Also, since an offset or noise due to the common mode component is reduced in the output of the amplifier 130, an accuracy of the output of the amplifier 130 may increase. Therefore, other circuit elements (for example, the ADC 140, a sample and hold circuit, and a chopper circuit), connected to the output of the amplifier 130 may be reduced and a wider operation range may be allowed.

As such, in a signal measuring circuit, performances required for circuit elements connected to the amplifier 130 and an output of the amplifier 130 through the reset unit 120 are reduced, so that each of the elements may be implemented in a simple structure and costs, power, and an area used for each of the elements are reduced.

In the following description, the bioimpedance to be measured is not in a form that largely changes from zero to a maximum value, but may be a form in which an impedance value changes within a minute change range based on a fixed impedance value of a large direct current (DC) component. Thus, the reset unit 120 removes a component corresponding to an undesired fixed impedance value, thereby reducing the magnitude of voltage input to the amplifier 130. Since the undesired component is removed by the reset unit 120, the signal measuring circuit may provide an additional amplifier gain with respect to the input voltage signal.

The ADC 140 outputs a digital signal indicating the impedance change of the target object 109 by converting the amplified signal to a digital form. The ADC 140 converts an analog value of the amplified value to a digital value, for example, digital codes including a bit sequence. The ADC 140 converts the amplified signal or a discrete signal to the digital form at a time point in a period of the current signal. A time point at which the ADC 140 performs digital conversion may vary based on a case in which a resistance value is to be acquired from an impedance and a case in which a reactance value is to be acquired from the impedance.

The clock generator 150 transfers a clock frequency and control signals to each elements of the signal measuring apparatus 100. For example, the clock generator 150 provides the carrier frequency to the power source 110. The clock generator 150 transfers a reset signal that activates a reset switch, to the reset unit 120. The clock generator 150 transfers, to the ADC 140, a signal indicating a measurement time point during the period corresponding to the carrier frequency.

Figure 2:
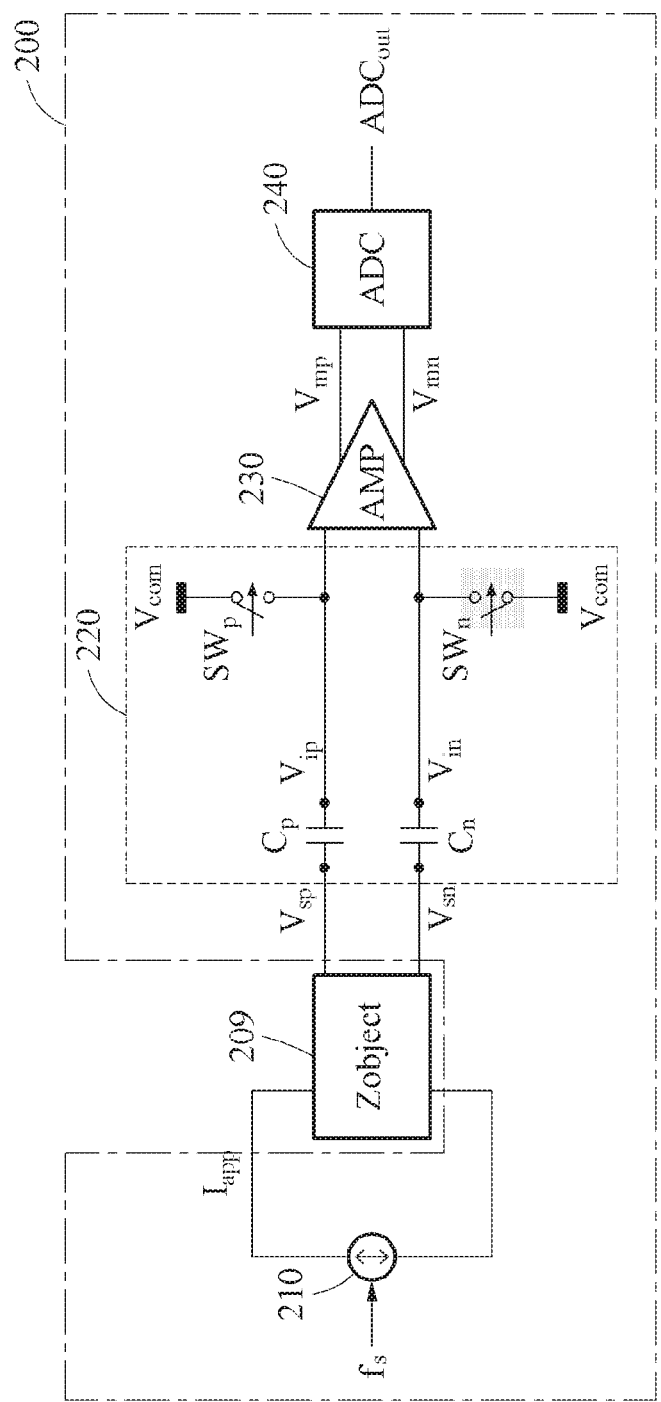
FIG. 2 is a circuit diagram illustrating an example of a signal measuring apparatus.

FIG. 2 is circuit diagram illustrating an example of a signal measuring apparatus.

A signal measuring apparatus 200 includes a power source 210, a reset unit 220, an amplifier 230, and an ADC 240. In the example of FIG. 2, a clock generator will be omitted for brevity of description.

The power source 210 generates a current signal $I_{app}$ having a known amplitude and a carrier frequency $f_s$. As illustrated in FIG. 2, the power source 210 supplies a current signal to a target object 209. The target object 209 has a target impedance $Z_{object}$. The target impedance $Z_{object}$ may be a sum of an impedance of the target object 209 and an impedance of an electrode in contact with the target object 209.

An object voltage signal $V_{sp}$, $V_{sn}$ is generated from the target object 209. The object voltage signal $V_{sp}$, $V_{sn}$ is transferred to the reset unit 220. FIG. 2 illustrates that the amplifier 230 is a full differential amplifier, a type of the amplifier 230 is not limited thereto. The amplifier 230 may also be implemented in a single ended mode.

The reset unit 220 includes a capacitor $C_p$, $C_n$ and a reset switch $SW_p$, $SW_n$. The capacitor $C_p$, On is connected between the target object 209 and the amplifier 230. The reset switch $SW_p$, $SW_n$ is connected between one end of the capacitor $C_p$, $C_n$ and a common mode node $V_{com}$ that supplies a common mode voltage. One end of a first capacitor, for example, the capacitor $C_p$ is connected to the target object 209, and an other end of the first capacitor $C_p$ is connected to a first input end and a first reset switch, for example, the reset switch $SW_p$ of the amplifier 230. One end of a second capacitor, for example, the capacitor $C_n$ is connected to the target object 209, and an other end of the second capacitor $C_n$ is connected to a second input end and a second reset switch, for example, the reset switch $SW_n$ of the amplifier 230. In an example, the reset switch $SW_p$, $SW_n$ is controlled by a reset signal. In following description, $V_{com}$ denotes both the common mode node and a common mode voltage supplied at the corresponding common mode node.

In the reset unit 220, the capacitor $C_p$, On having received the object voltage signal $V_{sp}$, $V_{sn}$ at the one end outputs an input voltage signal $V_{ip}$, $V_{in}$ to the input end of the amplifier 230. In an example, the input voltage signal $V_{ip}$, $V_{in}$ is changed following a change in the object voltage signal $V_{sp}$, $V_{sn}$. When the object voltage signal $V_{sp}$, $V_{sn}$ is changed, for example, increased or decreased by a first voltage variation from a first time point to a second time point during a period, the input voltage signal $V_{ip}$, $V_{in}$ is changed by the first voltage variation. In this example, the input voltage signal $V_{ip}$, $V_{in}$ is reset to have the common mode voltage $V_{com}$ at the second time point. When the object voltage signal $V_{sp}$, $V_{sn}$ is changed by a second voltage variation from the second time point to a third time point, the input voltage signal $V_{ip}$, $V_{in}$ is changed by the second voltage variation from the common mode voltage $V_{com}$. The first time point through the third time point, the first voltage variation, and the second voltage variation are provided for the purpose of understanding and not to be taken as being limited thereto. Waveform changes of the object voltage signal $V_{sp}$, $V_{sn}$ and the input voltage signal $V_{ip}$, $V_{in}$ will be described with reference to FIGS. 4, 6, and 8.

The amplifier 230 generates an amplified signal $V_{mp}$, $V_{mn}$ by amplifying the input voltage signal $V_{ip}$, $V_{in}$. The amplifier 230 outputs a first amplified signal $V_{mp}$ obtained by amplifying a first input voltage signal $V_{ip}$, and outputs a second amplified signal $V_{mn}$ obtained by amplifying a second input voltage signal $V_{in}$.

The ADC 240 is connected to an output end of the amplifier 230. The ADC 240 outputs a digital signal $ADC_{out}$ by converting the amplified signal $V_{mp}$, $V_{mn}$. The ADC 240 converts a differential amplified signal, for example, $V_{mp}$-$V_{mn}$ of the first amplified signal $V_{mp}$ and the second amplified signal $V_{mn}$ from an analog value to a digital value, thereby outputting the digital signal $ADC_{out}$ corresponding to the impedance change of the target object 209. As described above, Z=V/I, the current I is known, and the voltage V is acquired as a differential amplified signal. Thus, the ADC 240 outputs the digital signal $ADC_{out}$ corresponding to the impedance change by converting, to a digital value, the differential amplified signal acquired each time at which the current I has a peak value, for example, the amplitude in FIG. 2 supplied by the power source 210. Since the input voltage signal $V_{ip}$, $V_{in}$ is reset by the reset unit 220 and the amplitude thereof is reduced, the digital signal $ADC_{out}$ output by the ADC 240 represents a change in impedance.

Figure 3:
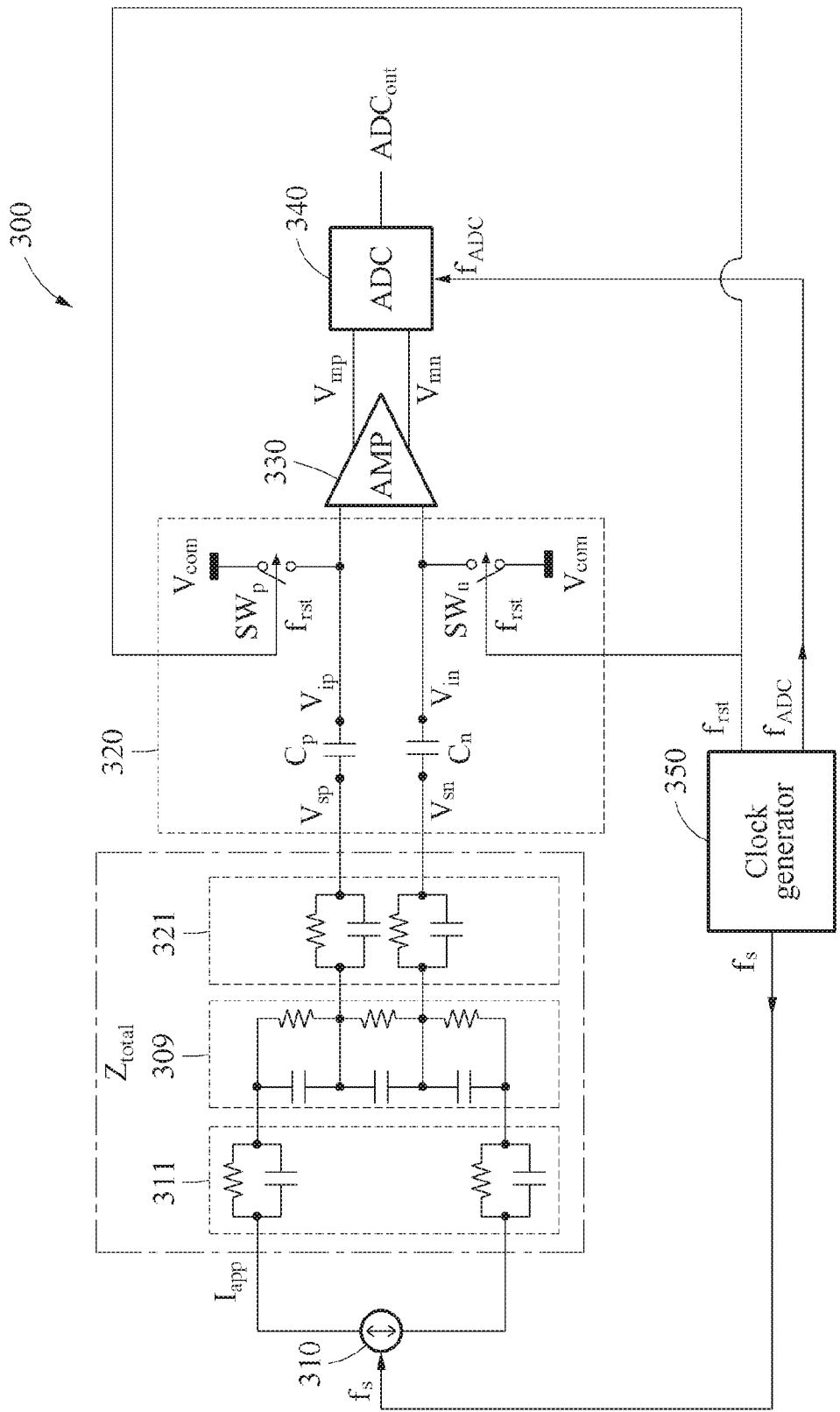
FIGS. 3 and 4 illustrate examples of a timing and a configuration of a signal measuring apparatus resetting an input voltage signal based on a timing.
Figure 4:
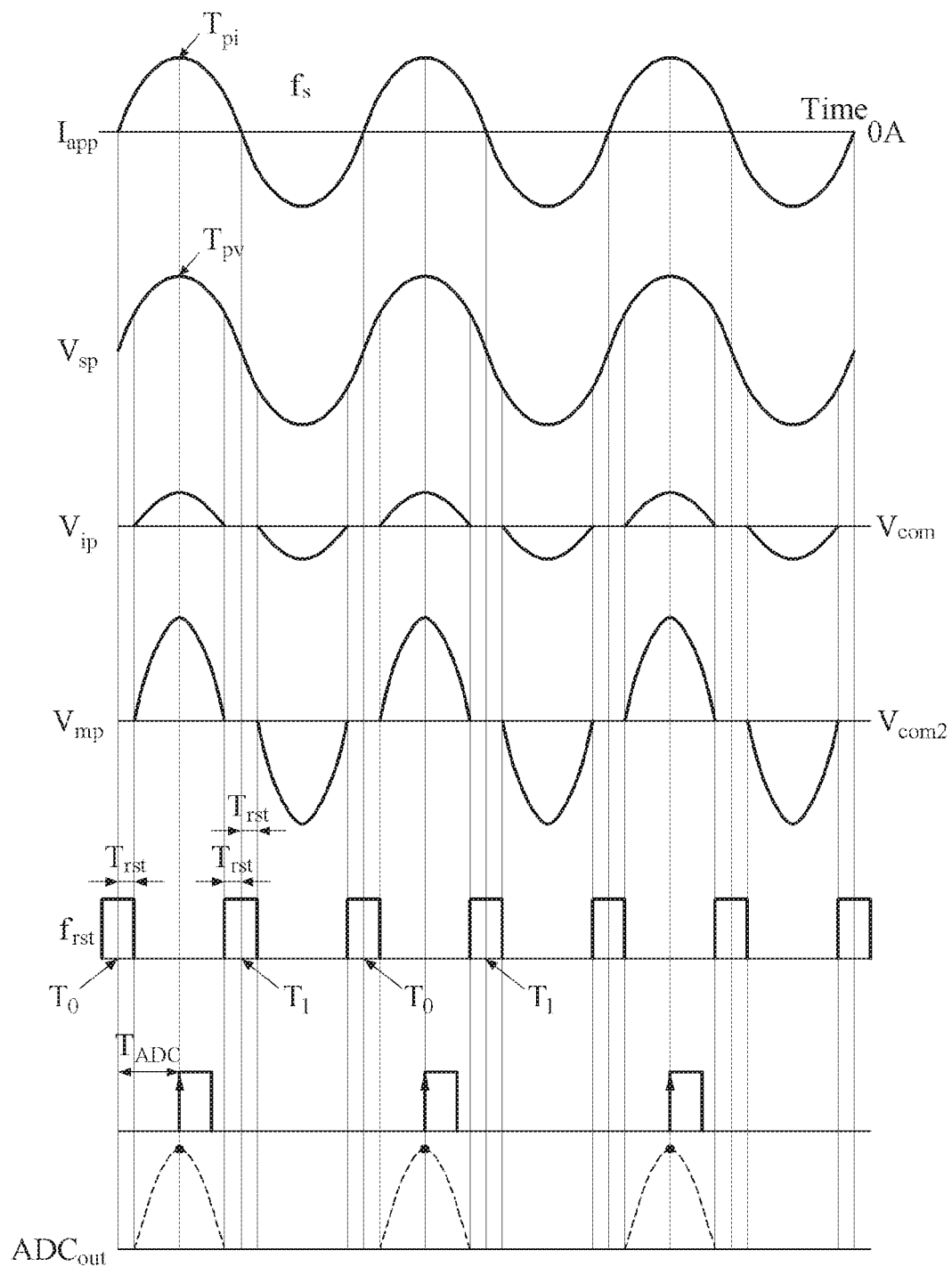

FIGS. 3 and 4 illustrate examples of a timing and a configuration of a signal measuring apparatus resetting an input voltage signal based on a timing.

FIG. 3 illustrates a structure of a signal measuring apparatus 300 outputting a digital signal corresponding to an impedance change each measurement time point determined in a period of a current signal supplied to a target object 309. FIG. 4 is a timing diagram illustrating an example of a signal waveform at a main node in the structure of FIG. 3. For ease and convenience of description, a positive end signal of a pair of signals in a differential mode will be mainly explained. The same explanation may be applied to a negative end signal.

A power source 310 supplies a current signal $I_{app}$ having an amplitude and a carrier frequency $f_s$ to the target object 309. In FIG. 4, a time point at which a current signal has a peak during a period corresponding to the carrier frequency fs is denoted as $T_{pi}$. The signal measuring apparatus 300 supplies the current signal to the target object 309 through a first electrode 311. Also, the signal measuring apparatus 300 receive an object voltage signal $V_{sp}$ from the target object 309 through a second electrode 321. The object voltage signal $V_{sp}$ may have a voltage applied to a total impedance $Z_{total}$ of impedances of the target object 309 and the first electrode 311 and the second electrode 321. The undesired fixed impedance of FIG. 1 may include impedances of the first electrode 311 and the second electrode 321 and an impedance that is not changed in the target object 309 irrespective of a biological activity and a biological condition.

FIG. 4 illustrates an example in which the object voltage signal $V_{sp}$ has a peak at a time point $T_{pv}$ during a period and the time point $T_{pv}$ is the same as a peck time point $T_{pi}$ of the current signal $I_{app}$ for ease of description. It is assumed that the total impedance $Z_{total}$ has a resistance value and does not have a reactance value. A phase of the object voltage signal $V_{sp}$ may vary in practice.

In an example, a clock generator 350 transfers a carrier frequency to the power source 310 and transfers a reset signal $f_{rst}$ to a reset unit 320. The clock generator 350 transfers the reset signal $f_{rst}$ to the reset unit 320 during a reset interval in the period. The clock generator 350 generates the reset signal $f_{rst}$ and a signal $f_{ADC}$ by controlling a phase with respect to the current signal.

When the reset signal $f_{rst}$ is transferred from the clock generator 350, the reset unit 320 resets an input voltage signal $V_{ip}$ to have a common mode voltage $V_{com}$. The reset unit 320 resets the input voltage signal $V_{ip}$ to have the common mode voltage $V_{com}$ during the reset interval determined in the period. For example, a reset switch $SW_p$ of the reset unit 320 connects the common mode node $V_{com}$ and an input end of an amplifier 330 during the reset interval in response to the reset signal $f_{rst}$, and disconnects the common mode node $V_{com}$ from the input end of the amplifier 330 when the reset interval elapses.

In FIG. 4, the reset signal $f_{rst}$ generated by the clock generator 350 indicates a magnitude corresponding to a high level logical value, for example, an H level logical value by an interval $T_{rst}$, for example, a reset interval before and after a reset time point $T_0$, $T_1$. In a remaining interval of the period, the reset signal $f_{rst}$ indicates a magnitude corresponding to a low level logical value, for example, an L level logical value.

The reset signal $f_{rst}$ indicates the H level logical value during the reset interval in the period. The reset switch is activated during the reset interval, so that the reset switch $SW_p$ is shorted and the common mode voltage $V_{com}$ is applied to the input end of the amplifier 330. Accordingly, the input voltage signal $V_{ip}$ is reset to have the common mode voltage $V_{com}$. As illustrated in FIG. 4, during the period in which the reset signal $f_{rst}$ indicates the H level logical value, the input voltage signal $V_{ip}$ has the common mode voltage $V_{com}$.

The reset signal $f_{rst}$ indicates the L level logical value in a remaining interval other than the reset interval in the period. During the interval in which the reset signal $f_{rst}$ indicates the L level logical value, the reset switch is inactivated so that a connection between both ends is blocked. In this example, the input voltage signal $V_{ip}$ is changed by a variation of the object voltage signal $V_{sp}$ based on the common mode voltage again, starting from a point in time at which the reset switch is inactivated.

Through the foregoing reset process, a desired impedance change range of the target object 309 is maintained, and a portion of a fixed impedance corresponding to a large value is removed.

After being reset, the amplifier 330 receives the input voltage signal $V_{ip}$ changing according to a change in the object voltage signal $V_{sp}$. For example, the amplifier 330 generates an amplified signal $V_{mp}$ by amplifying the input voltage signal $V_{ip}$ that has been reset at least once.

An ADC 340 generates the digital signal $ADC_{out}$ corresponding to an impedance change by converting the amplified signal $V_{mp}$ to a digital form. The clock generator 350 generates the signal $f_{ADC}$ indicating an operation of the ADC 340 for each measurement time point in the period. For example, the amplified signal $V_{mp}$ having an analog value is converted to a digital signal at a rising-edge time point of the signal $f_{ADC}$. The ADC 340 converts a differential signal $V_{mp}$-$V_{mn}$ of the amplified signals $V_{mp}$ and $V_{mn}$ to a digital signal. FIG. 4 illustrates a point in time at which an interval $T_{ADC}$ elapses as the rising-edge time point of the signal $f_{ADC}$, and the interval $T_{ADC}$ as a ¼ period. As described below, in an example, a resistance value having a real-number component may be acquired from impedances of the target object 309 at the rising-edge time point of the signal $f_{ADC}$ as shown in FIG. 4.

A point in time corresponding to the ¼ interval of the period is referred to as a 90-degree time point, a point in time corresponding to a ½ interval of the period is referred to as a 180-degree time point, a point in time corresponding to a ¾ interval of the period is referred to as a 270-degree time point, and a point in time corresponding to a 4/4 interval of the period is referred to as a 360-degree time point. The current signal given in the examples of FIGS. 3 and 4 has a sine waveform. Also, in the period, information of the 90-degree time point and the 270-degree time point indicate a real-number component and information of the 180-degree time point and the 360-degree time point indicate an imaginary number component. When the signal measuring apparatus 300 converts the amplified signal $V_{mp}$ each 90-degree time point of the period as illustrated in FIG. 4, the converted digital signal indicates a resistance value among impedances.

In FIG. 4, the zero-degree time point and the 180-degree time point are reset time points $T_0$ and $T_1$. The reset signal $f_{rst}$ of FIG. 4 has the H level logical value in an interval including the zero-degree time point and the 180-degree time point, and has the L level logical value in an interval including the 90-degree time point and the 270-degree time point. Since a maximum amplitude corresponding to the resistance value appears at the 90-degree time point and the 270-degree time point based on the sine waveform given as the current signal, the reset signal $f_{rst}$ of FIG. 4 may have a reset interval set to maintain a component corresponding to the resistance value among the impedance from the object voltage signal $V_{sp}$.

The signal measuring apparatus 300 is not limited to measuring only the resistance value among the impedances, and may measure a reactance value in accordance with a design. For example, the reset signal $f_{rst}$ has the L level logical value at the 180-degree time point and the 360-degree time point (the zero-degree time point) at which information corresponding to an imaginary number component appears. In this example, the ADC 340 converts the amplified signal $V_{mp}$ to a digital signal every zero-degree time point in the period, thereby acquiring a digital signal corresponding to the reactance value among the impedances.

Furthermore, the signal measuring apparatus 300 may acquire both the resistance value and the reactance value among the impedances. The reset unit 320 disconnects the common mode node $V_{com}$ from the input end of the amplifier 330 during an interval including a resistance measurement time point, for example, the 90-degree time point, and disconnects the common mode node $V_{com}$ from the input end of the amplifier 330 during an interval including a reactance measurement time point, for example, the zero-degree time point. Through this, the input voltage signal $V_{ip}$ maintains a resistance component and a reactance component. Also, the ADC 340 converts the amplified signal $V_{mp}$ to a digital form at the resistance measurement time point, thereby generating the digital signal $ADC_{out}$ corresponding to the resistance value among the impedances of the target object 309. The ADC 340 converts the amplified signal $V_{mp}$ to a digital form at the reactance measurement time point, thereby generating the digital signal $ADC_{out}$ corresponding to the reactance value among the impedances of the target object 309.

The signal measuring apparatus 300 acquires the resistance value and the reactance value among the impedances, sequentially or simultaneously. In one example, the signal measuring apparatus 300 acquires the resistance value in one period and the reactance value in a subsequent period. Thus, the resistance value and the reactance value are acquired in alternate periods. In another example, the signal measuring apparatus 300 connects a first ADC for outputting a digital signal corresponding to the resistance value from the amplified signal $V_{mp}$ and a second ADC for outputting a digital signal corresponding to the reactance value from the amplified signal $V_{mp}$ to the amplifier 330 in parallel.

Figure 5:
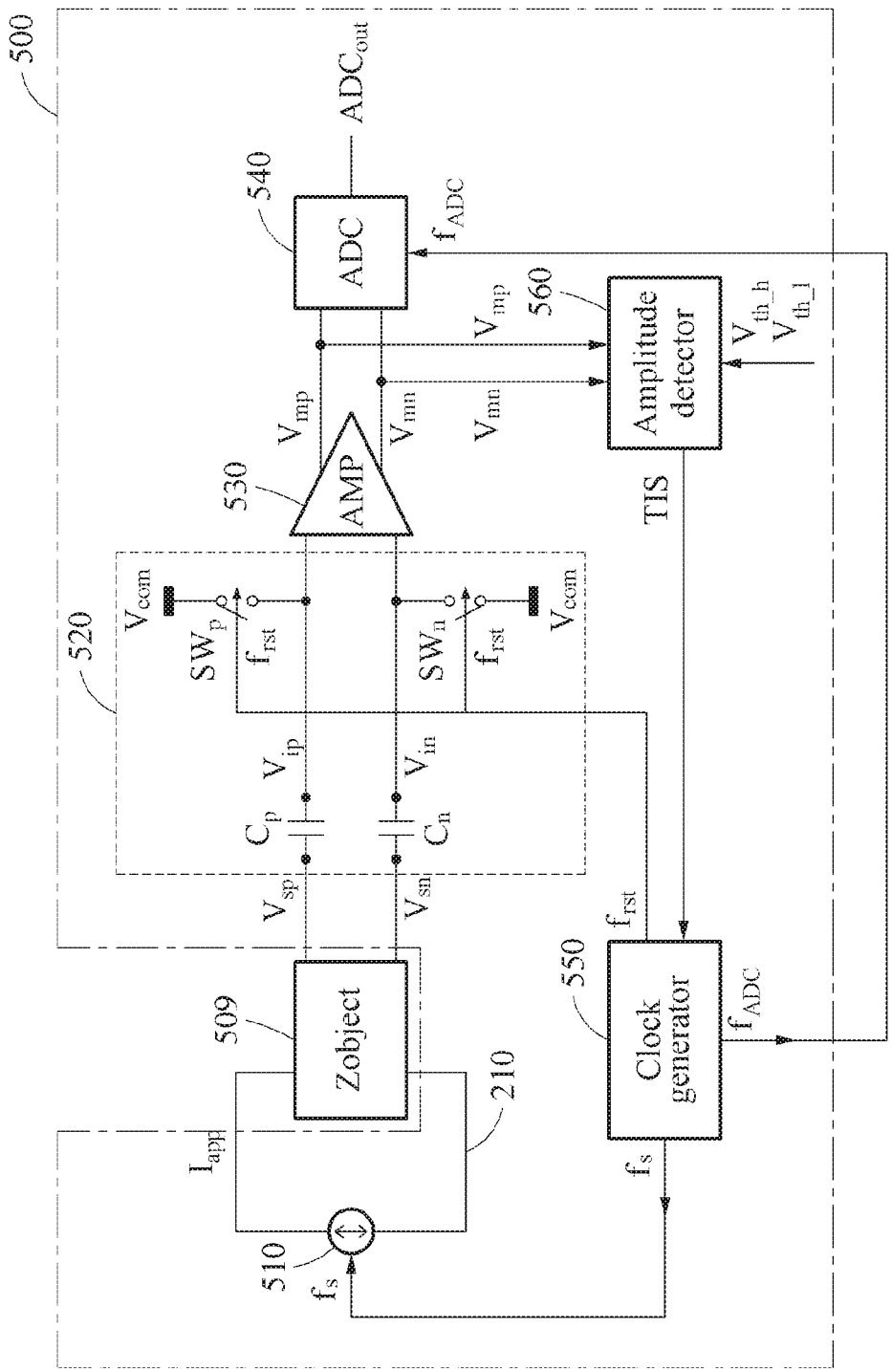
FIGS. 5 and 6 illustrate examples of a timing and a configuration of a signal measuring apparatus resetting an input voltage signal based on an amplitude.
Figure 6:
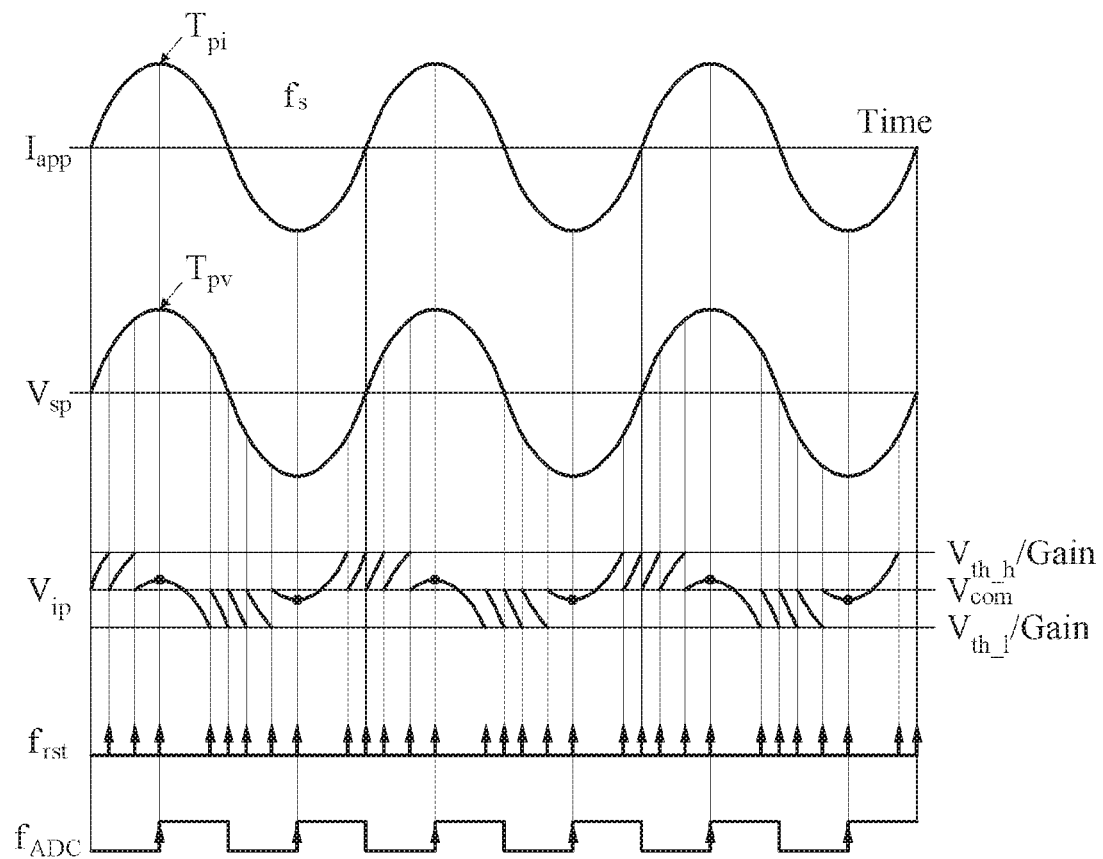

FIGS. 5 and 6 illustrate examples of a timing and a configuration of a signal measuring apparatus resetting an input voltage signal based on an amplitude.

The operations of the target object 309, the power source 310, the amplifier 330, and the ADC 340 described with reference to FIG. 3 are the same as or similar to those of a target object 509, a power source 510, an amplifier 530, and an ADC 540 in a signal measuring apparatus 500 and thus, in addition to the description of FIG. 5 below, the descriptions of FIGS. 1-4 are also applicable to FIG. 5 and are incorporated herein by reference. Thus, the above description may not be repeated here. The signal measuring apparatus 500 further includes an amplitude detector 560.

The amplitude detector 560 compares an amplitude of the amplified signal $V_{mp}$, $V_{mn}$ to a threshold voltage $V_{th\_h}$, $V_{th\_l}$. In response to the amplitude of the amplified signal $V_{mp}$, $V_{mn}$ touching the threshold voltage $V_{th\_h}$, $V_{th\_l}$, the amplitude detector 560 transfers a touch indication signal to a clock generator 550. For example, the amplitude detector 560 generates a touch indication signal TIS each time that the first amplified signal $V_{mp}$ touches one of the first threshold voltage, for example, the threshold voltage $V_{th\_h}$ and a second threshold voltage, for example, the threshold voltage $V_{th\_l}$. The clock generator 550 generates the reset signal $f_{rst}$ in response to the touch indication signal TIS. The amplitude detector 560 performs the same operation on the second amplified signal $V_{mn}$.

A reset unit 520 resets the input voltage signal $V_{ip}$, $V_{in}$ to have the common mode voltage $V_{com}$ each time that the amplified signal $V_{mp}$, $V_{mn}$ output from the amplifier 530 touches the threshold voltage $V_{th\_h}$, $V_{th\_l}$. For example, the reset unit 520 resets the input voltage signal $V_{ip}$, $V_{in}$ to have the common mode voltage Worn when the reset signal $f_{rst}$ is transferred from the clock generator 550. In response to the reset signal $f_{rst}$, the reset switch $SW_p$, $SW_n$ of the reset unit 520 connects the common mode node $V_{com}$ and an input end of the amplifier 530 during a period and disconnects the input end of the amplifier 530 from the common mode node $V_{com}$ during a remaining interval of the period.

In FIG. 6, since a waveform of the amplified signal $V_{mp}$ is the same as a waveform of the input voltage signal $V_{ip}$ except for a magnitude, the waveform of the amplified signal $V_{mp}$ is omitted. Although FIG. 6 illustrates threshold voltages $V_{th\_h}$/Gain and $V_{th\_l}$/Gain reduced by a gain for the input voltage signal $V_{ip}$ for ease of description, the amplitude detector 560 may actually compare the amplified signal $V_{mp}$, V. and the threshold voltage $V_{th\_h}$, $V_{th\_l}$ as described above. Since the signal having been amplified is used, the performance required for the amplitude detector 560 may also be reduced.

As illustrated in FIG. 6, each time the amplified signal $V_{mp}$, $V_{mn}$ touches the threshold voltage $V_{th\_h}$, $V_{th\_l}$, the input voltage signal $V_{ip}$ is reset to have the common mode voltage $V_{com}$. Accordingly, a magnitude of the input voltage signal $V_{ip}$ input to the amplifier 530 may be compressed.

The ADC 540 generates a digital signal corresponding to a resistance value among impedances of the target object by converting the amplified signal $V_{mp}$, $V_{mn}$ to a digital form at a resistance measuring time point, for example, a 90-degree time point and a 270-degree time point. The ADC 540 generates a digital signal corresponding to a reactance value among the impedances of the target object by converting the amplified signal $V_{mp}$, $V_{mn}$ to a digital form at a reactance measuring time point, for example, a zero-degree time point and a 180-degree time point. The ADC 540 may generate the digital signals corresponding to the resistance value and the reactance value in sequence or in parallel.

Also, the signal measuring apparatus counts a touch number of times that an amplitude of the amplified signal $V_{mp}$, $V_{mn}$ reaches the threshold voltage $V_{th\_h}$, $V_{th\_l}$. For example, in FIG. 6, the amplified signal $V_{mp}$, $V_{mn}$ reaches the threshold voltage $V_{th\_h}$, $V_{th\_l}$ eight times in one period. The signal measuring apparatus calculates an original amplitude of the amplified signal $V_{mp}$, $V_{mn}$ from the counted touch number and the threshold voltage $V_{th\_h}$, $V_{th\_l}$.

For example, since a signal value acquired at a measurement time point is obtained from the amplified signal $V_{mp}$, $V_{mn}$ having a magnitude reduced by the reset unit 520, information associated with an original impedance absolute value may not be included. The signal measuring apparatus restores the original impedance absolute value from the counted total number and the threshold voltage $V_{th\_h}$, $V_{th\_l}$.

In FIG. 6, the input voltage signal $V_{ip}$ reaches an upper threshold, for example, $V_{th\_h}$/Gain two times after the zero-degree time point, so that a reset operation is performed two times. After that, the signal measuring apparatus converts a value, $V_{ip\_}90°$ of the input voltage signal $V_{ip}$ at the 90-degree time point from analog to digital. Through this, the original impedance absolute value of the 90-degree time point is calculated to be, for example, Vip_abs_90°=Vip_90°+2×Vth_h/Gain. Also, the input voltage signal $V_{ip}$ reaches a lower threshold, for example, $V_{th\_l}$/Gain four times, so that the reset operation is performed four times. After that, the signal measuring apparatus converts a value $V_{ip\_}270°$ of the input voltage signal $V_{ip}$ at the 270-degree time point from analog to digital. Through this, the original impedance absolute value of the 270-degree time point is calculated to be, for example, Vip_abs_270°=Vip_270°−4×Vth_l/Gain. When the reset and the aforementioned operation are repeated each time that a value of an applied current is zero, an absolute value of the input voltage signal $V_{ip}$ is acquired for each period.

Figure 7:
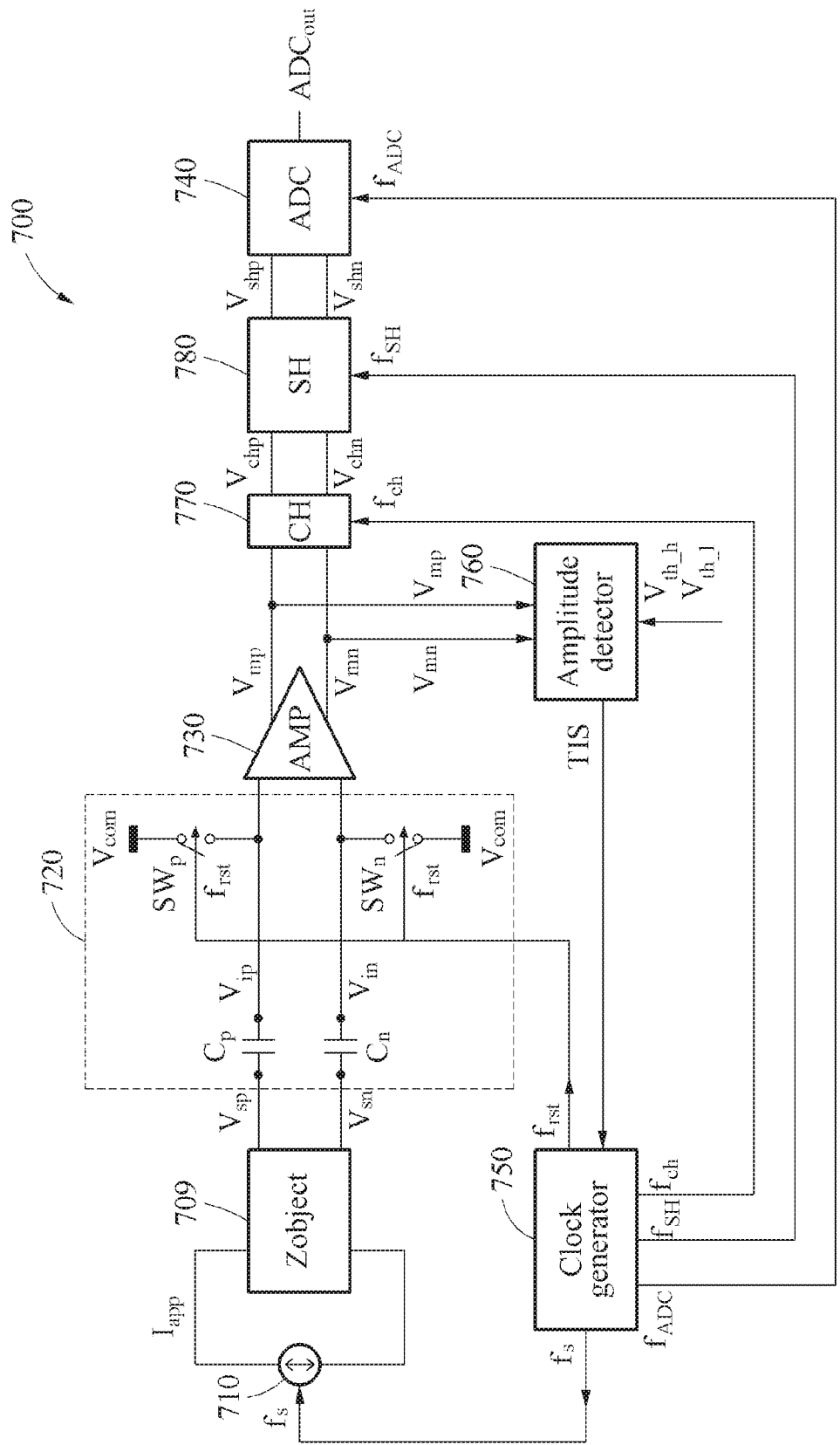
FIGS. 7 and 8 illustrate examples of a timing and a configuration of a signal measuring apparatus further including a chopper circuit and a sample and hold circuit.
Figure 8:
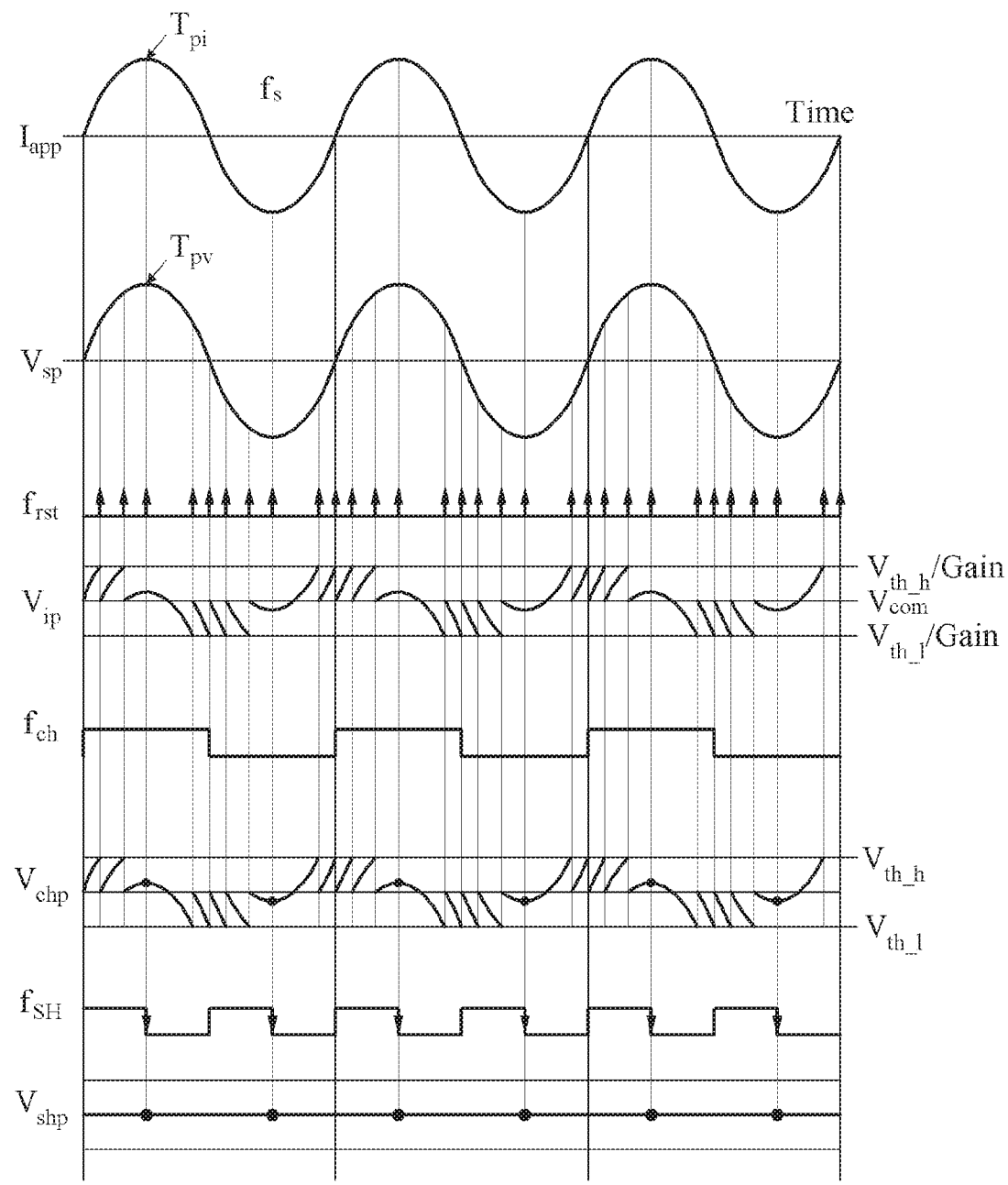

FIGS. 7 and 8 illustrate a timing and a configuration of a signal measuring apparatus further including a chopper circuit and a sample and hold circuit.

The operations of the target object 509, the power source 510, the reset unit 520, the amplifier 530, the ADC 540, the clock generator 550, and the amplitude detector 560 described with reference to FIG. 5 are the same as or similar to those of a target object 709, a power source 710, a reset unit 720, an amplifier 730, an ADC 740, a clock generator 750, and an amplifier detector 760 in a signal measuring apparatus 700 and thus, in addition to the description of FIG. 7 below, the descriptions of FIGS. 1-6 are also applicable to FIG. 7 and are incorporated herein by reference. Thus, the above description may not be repeated here.

The signal measuring apparatus 700 further includes a chopper circuit 770 and a sample and hold circuit 780 between the amplifier 730 and the ADC 740. In an example, the amplifier 730 may be implemented as a differential amplifier.

The chopper circuit 770 is connected to an output end of the differential amplifier 730. The chopper circuit 770 generates a chopper voltage signal $V_{chp}$, $V_{chn}$ by alternately switching connections between two output nodes of the amplifier 730 and two input nodes of the sample and hold circuit 780 each half period of a carrier frequency, for example, a 180-degree time point in the period. For example, during a first half period of the period, the chopper circuit 770 connects a first output node of the amplifier 730 to a first input node of the sample and hold circuit 780 and connects a second output node of the amplifier 730 to a second input node of the sample and hold circuit 780. During a second half period of the period, the chopper circuit 770 connects the first output node of the amplifier 730 to the second input node the sample and hold circuit 780 and connects the second output node of the amplifier 730 to the first input node of the sample and hold circuit 780. Through this, as illustrated in FIG. 8, the chopper circuit 770 generates a positive differential chopper signal $V_{chp}$-$V_{chn}$ in an interval in which the differential input signal $V_{ip}$-$V_{in}$ is negative, for example, a 270-degree time point in FIG. 8. Thereafter, on a later stage, the ADC 740 may convert information corresponding to the 90-degree time point and information corresponding to the 270-degree time point into a digital form.

The sample and hold circuit 780 is connected to an output end of the chopper circuit 770. The sample and hold circuit 780 samples a chopper voltage signal $V_{chp}$, $V_{chn}$ during a sampling interval in the period and hold the sampled signal during a holding interval, thereby generating a discrete signal $V_{shp}$, $V_{shn}$. In an example, the sampling interval is determined before each measurement time point in the period and the holding interval is determined after each measurement time point in the period. In the example of FIG. 8, the sampling interval includes an interval between the zero-degree time point and the 90-degree time point and an interval between the 180-degree time point and the 270-degree time point. Also, the holding interval includes an interval between the 90-degree time point and the 180-degree time point and an interval between the 270-degree time point and a 360-degree time point.

The ADC 740 is connected to an output end of the sample and hold circuit 780. The ADC 740 converts, to a digital signal, a differential discrete signal $V_{shp}$-$V_{shn}$ between a first discrete signal, for example, the discrete signal $V_{shp}$ and a second discrete signal, for example, the discrete signal $V_{shn}$ output from the sample and hold circuit 780.

Figure 9:
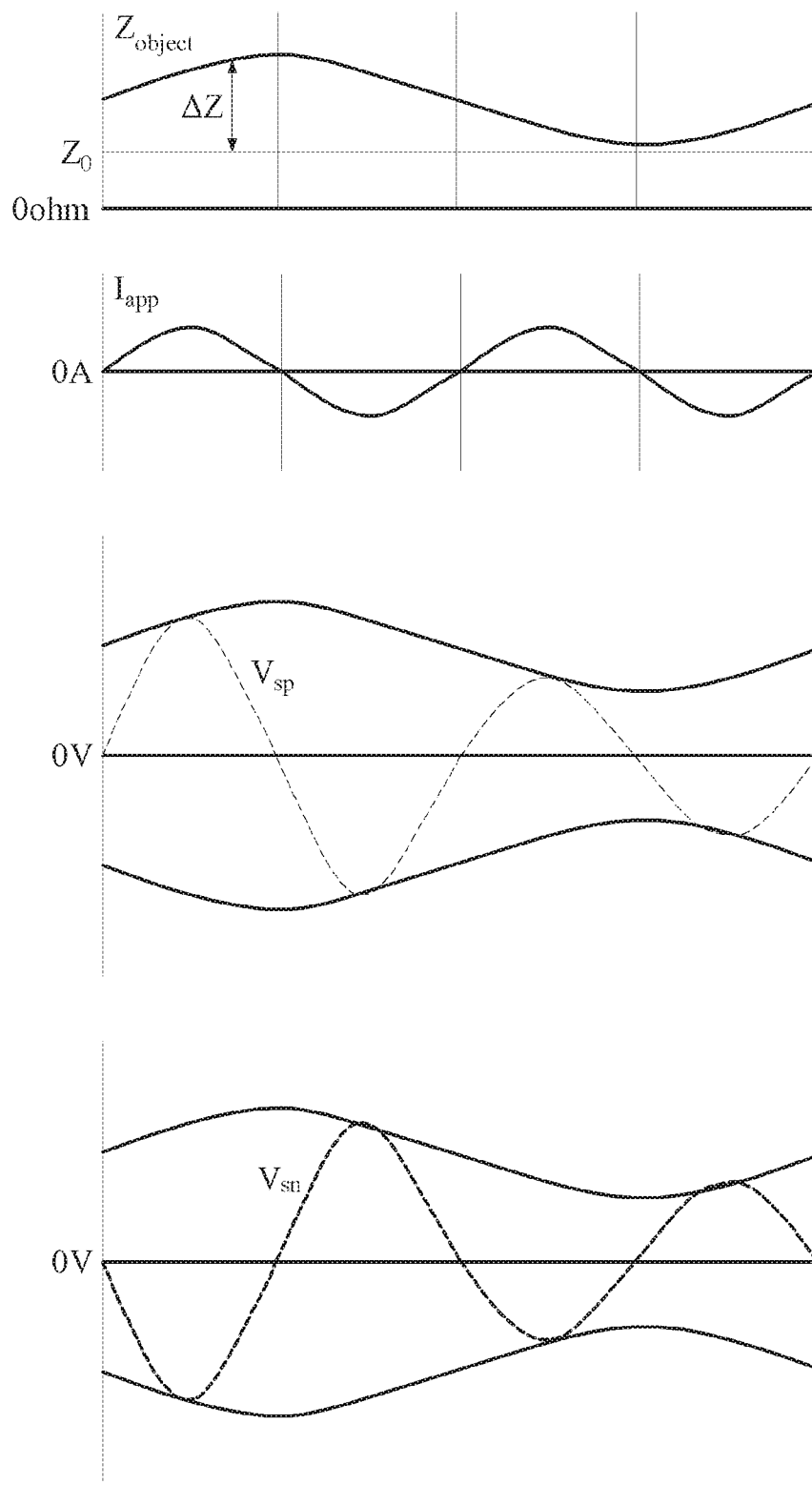
FIGS. 9 and 10 illustrate examples of a signal measuring process.
Figure 10:
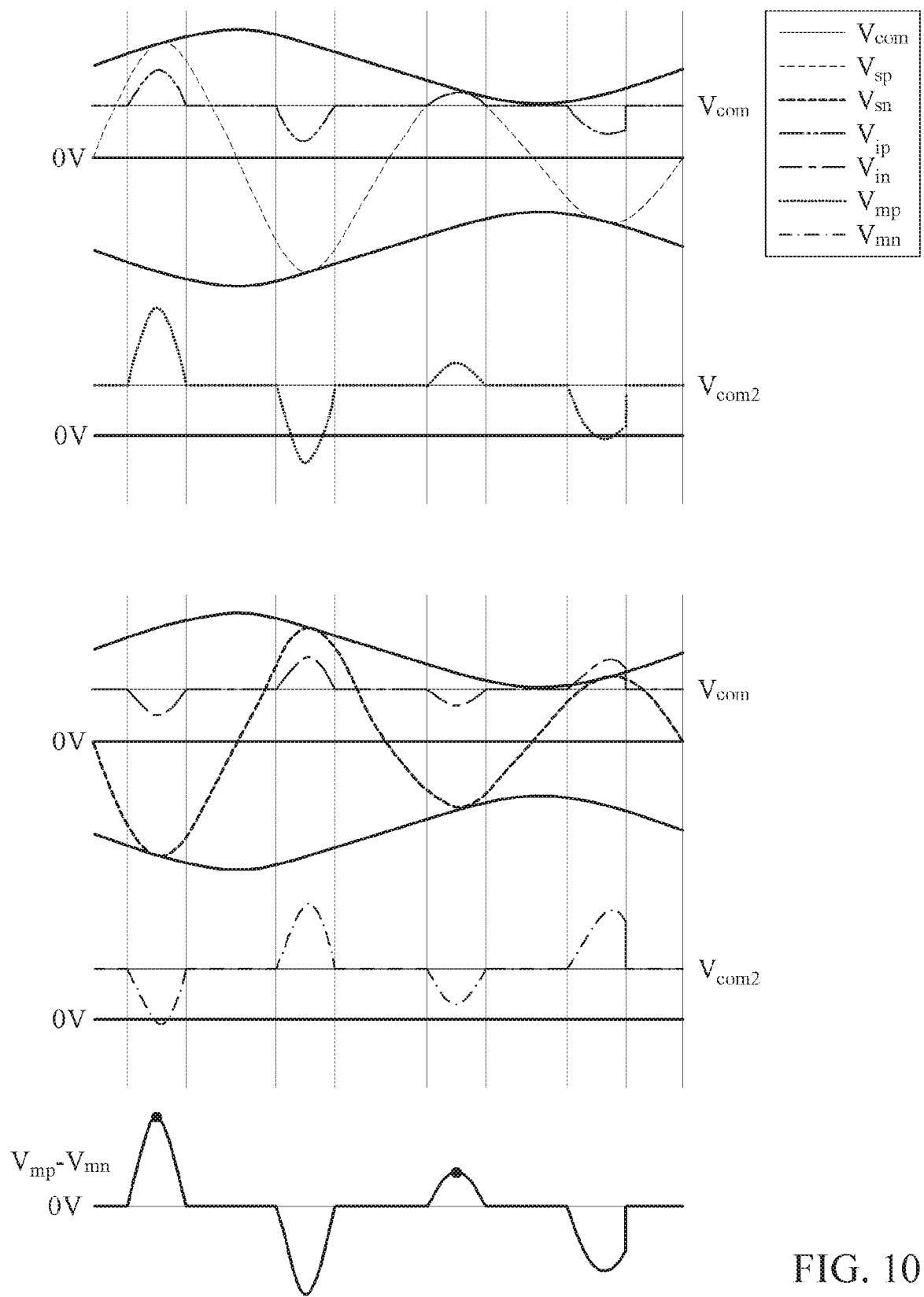

FIGS. 9 and 10 illustrate examples of measuring a signal.

For brevity of description, the examples in which the impedance is fixed are described with reference to FIGS. 4, 6, and 8. In actual implementation, an impedance of a target object may be changed. Referring to FIG. 9, a carrier frequency of a current signal supplied by a power source may be at least twice a frequency of an object impedance. FIG. 9 illustrates a change in object impedance. The object impedance is modeled as shown in Equation 1.

$$Z_{object} = Z_0 + \Delta Z \qquad \text{[Equation 1]}$$

In Equation 1, $Z_0$ denotes an undesired fixed impedance, $\Delta Z$ denotes a change amount of impedance corresponding to an object of interest, and $Z_{object}$ denotes a total impedance of an object. As described with reference to FIG. 1, a high-resolution ADC is required for amplification performed using a gain. However, there is an inefficiency issue that a non-interest region $Z_0$ accounts for most of a dynamic input range of an amplifier. As described with reference to FIGS. 1 through 8, a signal measuring apparatus removes a portion corresponding to a fixed impedance through a reset operation performed based on a common mode voltage.

When the signal measuring apparatus supplies the current signal $I_{app}$ to a target object, according to Ohm's law, an object voltage signal $V_{sp}$, $V_{sn}$ is generated as a synthesized signal of the current signal $I_{app}$ and the total impedance $Z_{object}$ of the target object. As illustrated in FIG. 9, an envelope of the object voltage signal $V_{sp}$, $V_{sn}$ corresponds to the total impedance $Z_{object}$ of the target object.

Referring to FIG. 10, an input voltage signal $V_{ip}$, $V_{in}$ and an amplified signal $V_{mp}$, $V_{mn}$ are generated through the operations described with reference to FIGS. 3 and 4. The input voltage signal $V_{ip}$, $V_{in}$ has a waveform that swings based on the common mode voltage $V_{com}$. The amplified signal $V_{mp}$, $V_{mn}$ has a waveform that swings based on another common signal $V_{com2}$.

As illustrated in FIG. 10, an ADC generates a digital signal by converting a differential amplified signal $V_{mp}$-$V_{mn}$ at the 90-degree time point and the 270-degree time point. In FIG. 10, a point of an analog signal converted by the ADC is indicated by a point. Here, an envelope of the differential amplified signal $V_{mp}$-$V_{mn}$ changes based on a variation of the total impedance $Z_{object}$ of the object described with reference to FIG. 9. Thus, a final output digital signal may also represent the variation of the total impedance $Z_{object}$ of the object.

Figure 11:
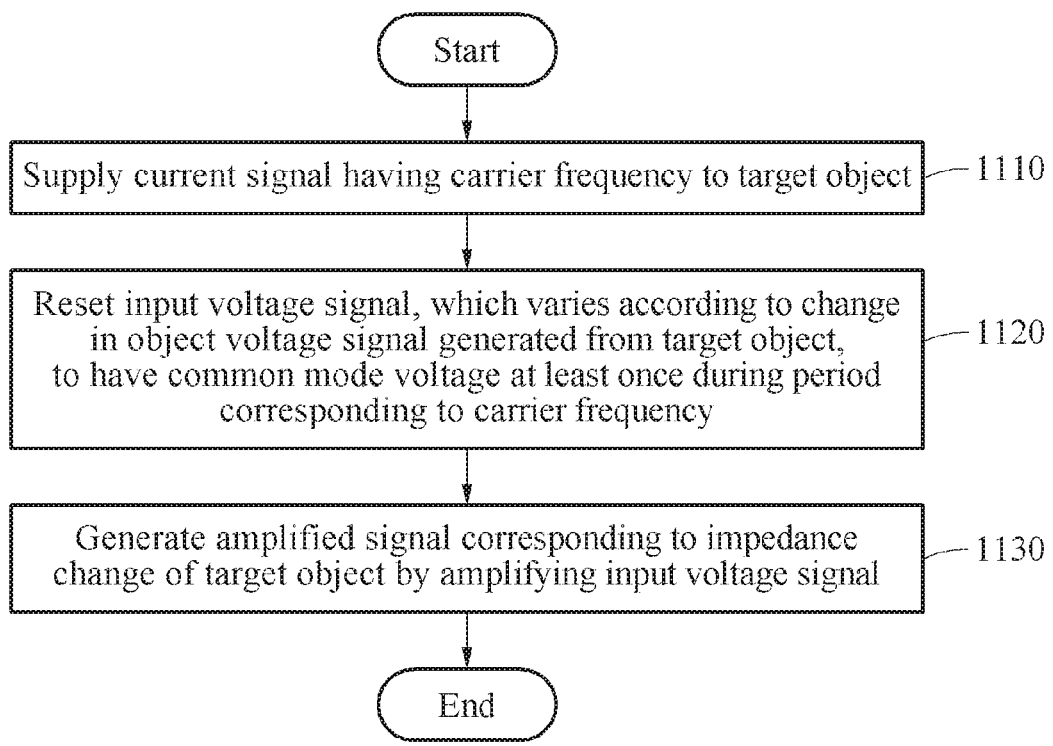
FIG. 11 is a diagram illustrating an example of a signal measuring method.

FIG. 11 is a diagram illustrating an example of a signal measuring method. The operations in FIG. 11 may be performed in the sequence and manner as shown, although the order of some operations may be changed or some of the operations omitted without departing from the spirit and scope of the illustrative examples described. Many of the operations shown in FIG. 11 may be performed in parallel or concurrently. One or more blocks of FIG. 11, and combinations of the blocks, can be implemented by special purpose hardware-based computer, such as a processor, that perform the specified functions, or combinations of special purpose hardware and computer instructions. In addition to the description of FIG. 11 below, the descriptions of FIGS. 1-10 are also applicable to FIG. 11 and are incorporated herein by reference. Thus, the above description may not be repeated here.

In operation 1110, a power source supplies a current signal having a carrier frequency to a target object.

In operation 1120, a reset unit resets an input voltage signal, which is changed according to a change in an object voltage signal generated from the target object receiving the current signal, to have a common mode voltage at least once during a period corresponding to the carrier frequency.

In operation 1130, an amplifier generates an amplified signal by amplifying the input voltage signal.

An ADC of the signal measuring apparatus outputs a digital signal corresponding to an impedance change from the amplified signal generated in operation 1130.

The signal measuring method is not limited to the example of FIG. 11, and one or more operations described with reference to FIGS. 1 through 10 may be performed simultaneously or in parallel.

The reset unit and other apparatuses, units, modules, devices, and other components described herein are implemented by hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In an example, the instructions or software includes at least one of an applet, a dynamic link library (DLL), middleware, firmware, a device driver, an application program storing the method of measuring a signal. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EEPROM), random-access memory (RAM), dynamic random access memory (DRAM), static random access memory (SRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, card type memory such as multimedia card, secure digital (SD) card, or extreme digital (XD) card, magnetic tapes, floppy disks, magneto-optical data storage devices, optical data storage devices, hard disks, solid-state disks, and any other device that is configured to store the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An apparatus for measuring a signal, the apparatus comprising:
    a power source configured to supply a current signal having a carrier frequency to a target object;
    a reset circuit configured to change, at least once during a reset interval using a switch, a first input connection of an amplifier, connected to an input voltage signal, to a second input connection of the amplifier, connected to a reference voltage,
    wherein the switch is configured to switch between the first input connection of the amplifier and the second input connection of the amplifier, and
    wherein the input voltage signal is changed according to a change in an object voltage signal generated from the target object receiving the current signal; and
    the amplifier configured to generate an amplified signal by amplifying the input voltage signal being reset,
    wherein the reset circuit comprises:
    a capacitor configured to connect the target object and the amplifier; and
    for the switching between the first input connection of the amplifier and the second input connection of the amplifier, the switch configured to connect one end of the capacitor and a common mode node that supplies the reference voltage in case of being switched to the second input connection of the amplifier.

2. The apparatus of claim 1, further comprising:
    an analog-to-digital converter connected to an output end of the amplifier.

3. The apparatus of claim 2, wherein the analog-to-digital converter is configured to output a digital signal indicating an impedance change of the target object by converting the amplified signal to a digital form.

4. The apparatus of claim 1, further comprising:

a clock generator configured to transfer the carrier frequency to the power source and to transfer a reset signal to the reset circuit, wherein the reset circuit is further configured to reset the input voltage signal to a common mode reference signal in response to the reset signal being transferred from the clock generator, and wherein the amplifier is further configured to receive the input voltage signal that is changed according to a change in the object voltage signal after being reset.

5. The apparatus of claim 1, wherein the reset circuit is further configured to reset the input voltage signal to have the reference voltage during the reset interval.

6. The apparatus of claim 5, further comprising:

a clock generator configured to transfer a reset signal during the reset interval, wherein the reset circuit comprises:

the switch configured to connect an input end of the amplifier and a common mode node, that supplies the reference voltage, during the reset interval, in response to the reset signal indicating changing from the first input connection to the second input connection of the amplifier and to disconnect the common mode node from the input end of the amplifier, in response to the reset interval elapsing.

7. The apparatus of claim 6, wherein the reset circuit is further configured to disconnect the common mode node from the input end of the amplifier during an interval including a resistance measuring time point and to disconnect the common mode node from the input end of the amplifier during an interval including a reactance measuring time point.

8. The apparatus of claim 7, further comprising:

an analog-to-digital converter configured to generate a digital signal corresponding to a resistance value among impedances of the target object by converting the amplified signal to a digital form at the resistance measuring time point, and to generate a digital signal corresponding to a reactance value among impedances of the target object by converting the amplified signal to a digital form at the reactance measuring time point.

9. The apparatus of claim 1, wherein the reset circuit is further configured to reset the input voltage signal to have the reference voltage each time an the amplified signal output from the amplifier reaches a threshold voltage.

10. The apparatus of claim 9, further comprising:

an amplitude detector configured to compare an amplitude of the amplified signal and the threshold voltage and to transfer a touch indication signal to a clock generator in response to the amplitude of the amplified signal reaching the threshold voltage; and the clock generator configured to generate a reset signal, in response to the touch indication signal, wherein the reset circuit is further configured to connect an input end of the amplifier and a common mode node, that supplies the reference voltage, in response to the reset signal during a period indicating changing from the first input connection to the second input connection of the amplifier and to disconnect the common mode node from the input end of the amplifier during a remaining interval of the period.

11. The apparatus of claim 9, wherein the apparatus is configured to count a touch number of times that an amplitude of the amplified signal touches the threshold voltage and to determine an original amplitude of the amplified signal calculated from the amplitude of the amplified signal using the counted touch number and the threshold voltage.

12. The apparatus of claim 1, further comprising:

an analog-to-digital converter configured to generate a digital signal corresponding to a resistance value among impedances of the target object by converting the amplified signal to a digital form at a resistance measuring time point, and to generate a digital signal corresponding to a reactance value among impedances of the target object by converting the amplified signal to a digital form at a reactance measuring time point.

13. The apparatus of claim 1, wherein the amplifier comprises:

a differential amplifier, and the apparatus further comprises:

a chopper circuit connected to an output end of the differential amplifier;

a sample and hold circuit connected to an output end of the chopper circuit; and an analog-to-digital circuit connected to an output end of the sample and hold circuit.

14. The apparatus of claim 13, wherein the chopper circuit is configured to generate a chopper voltage signal by alternately switching connections between two output nodes of the amplifier and two input nodes of the sample and hold circuit each half period of the carrier frequency.

15. The apparatus of claim 14, wherein the sample and hold circuit is configured to generate a discrete signal by sampling the chopper voltage signal during a sampling interval in a period corresponding to the carrier frequency and to hold a sampled signal during a holding interval, the sampling interval is an interval before each measurement time point in the period, and the holding interval is an interval after each measurement time point in the period.

16. The apparatus of claim 13, wherein the analog-to-digital circuit is further configured to convert a differential discrete signal between a first discrete signal and a second discrete signal output from the sample and hold circuit to a digital signal.

17. A method of measuring a signal, the method comprising:

supplying, by a power source, a current signal having a carrier frequency to a target object;

changing, at least once during a reset interval by a reset circuit and using a switch, a first input connection of an amplifier, connected to an input voltage signal, to a second input connection of the amplifier, connected to a common mode reference voltage, wherein the switch being configured to switch between the first input connection of the amplifier and the second input connection of the amplifier, and wherein input voltage signal is changed according to a change in an object voltage signal generated from the target object receiving the current signal; and generating, by the amplifier, an amplified signal corresponding to an impedance change of the target object by amplifying the input voltage signal being reset, wherein the reset circuit comprises a capacitor configured to connect the target object and the amplifier, and wherein the switching between the first input connection of the amplifier and the second input connection of the amplifier includes connecting one end of the capacitor and a common mode node that supplies the reference voltage in case of being switched to the second input connection of the amplifier.

* * * * *